United States Patent [19]

Alizon et al.

[11] Patent Number: 5,578,715

[45] Date of Patent: *Nov. 26, 1996

[54] METHODS, KITS, AND PROBES FOR DIAGNOSING HIV-2

[75] Inventors: Marc Alizon, Paris; Luc Montagnier, Le Plessy Robin; Denise Guetard; Francois Clavel, both of Paris; Pierre Sonigo; Mireille Guyader, both of Paris, all of France

[73] Assignee: Institut Pasteur, Paris, France

[ * ] Notice: The portion of the term of this patent subsequent to Sep. 24, 2008, has been disclaimed.

[21] Appl. No.: 754,903

[22] Filed: Sep. 4, 1991

Related U.S. Application Data

[60] Division of Ser. No. 3,764, Jan. 16, 1987, Pat. No. 5,051,496, which is a continuation-in-part of Ser. No. 933,184, Nov. 21, 1986, abandoned, which is a continuation-in-part of Ser. No. 916,080, Oct. 6, 1986, abandoned, and Ser. No. 835,228, Mar. 3, 1986, Pat. No. 4,839,288.

[30] Foreign Application Priority Data

| Jan. 22, 1986 | [FR] | France | 86 00910 |
| Jan. 22, 1986 | [FR] | France | 86 00911 |
| Feb. 6, 1986 | [FR] | France | 86 01635 |
| Feb. 13, 1986 | [FR] | France | 86 01985 |

[51] Int. Cl.$^6$ .................................................. C07H 21/04
[52] U.S. Cl. ........................... 536/23.72; 536/24.32; 435/5
[58] Field of Search ........................... 435/5; 536/23.72, 536/24.32

[56] References Cited

U.S. PATENT DOCUMENTS

| 4,629,783 | 12/1986 | Cosand | 530/344 |
| 4,839,288 | 6/1989 | Montagnier et al. | 435/235 |
| 5,051,496 | 9/1991 | Alizon et al. | 530/324 |
| 5,079,342 | 1/1992 | Alizon et al. | 530/324 |
| 5,223,423 | 6/1993 | Franchini et al. | 435/236 |

FOREIGN PATENT DOCUMENTS

| 0316695B1 | 3/1993 | European Pat. Off. . |
| WO85/04897 | 11/1985 | WIPO . |

OTHER PUBLICATIONS

Clavel et al., *Science* 233,343–346 (18 Jul. 1986a).
Clavel et al., *Nature* 324, 691–695 (18 Dec. 1986b).
Guyader et al., *Nature* 326,662–699 (16 Apr. 1987).

L. Stryer, *Biochemistry*, pp. 761–763 (W. H. Freeman and Company, San Francisco, 1975).

Wang et al., "Detection of Antibodies to Human T-lymphotropic Virus Type III by Using a Synthetic Peptide of 21 Amino Acid Residues Corresponding to a Highly Antigenic Segment of qp41 Envelope Protein", *Proc. Natl. Acad. Sci., USA*, 83, 6159–6163 (1986).

Chakrabarti et al., "Sequence of Simian Immunodeficiency Virus from Macaque and Its Relationship to Other Human and Simian Retroviruses", *Nature*, 328, 543–547 (1987).

Kanki et al., "Seroloqic Identification and Characterization of a Macaque T-lymphotropic Retrovirus Closely Related to HTLV-III," *Science*, 228, pp. 1199–1201 (1985).

Clavel et al., "LAV Type II: A Second Retrovirus Associated With AIDS In West Africa," *C. R. Acad. Sc. Paris*, Serie III, 302, pp. 485–488 (1986).

Klatzmann et al., "T-lymphocyte T4 Molecule Behaves As The Receptor For Human Retrovirus LAV,"*Nature*, 312, pp. 767–768 (1984).

Daniel et al., "Isolation of T-Cell Tropic HTLV-III-like Retrovirus from Macaques,"*Science*, 228, pp. 1201–1204 (1985).

Barin et al., "Seroloqical Evidence For Virus Related To Simian T-lymphotropic Retrovirus III in Residents of West Africa," *The Lancent*, pp. 1387–1389 (Dec. 21/28, 1985).

Sandstrom et al., "Antiviral Therapy In AIDS Clinical Pharmacoloqical Properties and Therapeutic Experience to Date," *Drugs*, 34, pp. 372–390 (1987).

Mitsuya et al., "Protection of T Cells Against Infectivity and Cytopathic Effect of HTLV-III *In Vitro*," Retroviruses in Human Lymphoma/Leukemia, M. Miwa et al., eds., pp. 277–288 (Japan Science Press, Tokyo, 1985).

*Primary Examiner*—Stephanie W. Zitomer
*Assistant Examiner*—Kenneth R. Horlick
*Attorney, Agent, or Firm*—Finnegan, Henderson, Farabow, Garrett & Dunner, L.L.P.

[57] ABSTRACT

A method for diagnosing an HIV-2 (LAV-II) infection and a kit containing reagents for the same is disclosed. These reagents include cDNA probes which are capable of hybridizing to at least a portion of the genome of HIV-2. In one embodiment, the DNA probes are capable of hybridizing to the entire genome of HIV-2. These reagents also include polypeptides encoded by some of these DNA sequences.

2 Claims, 5 Drawing Sheets

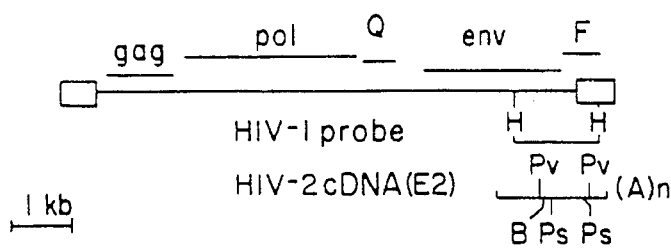

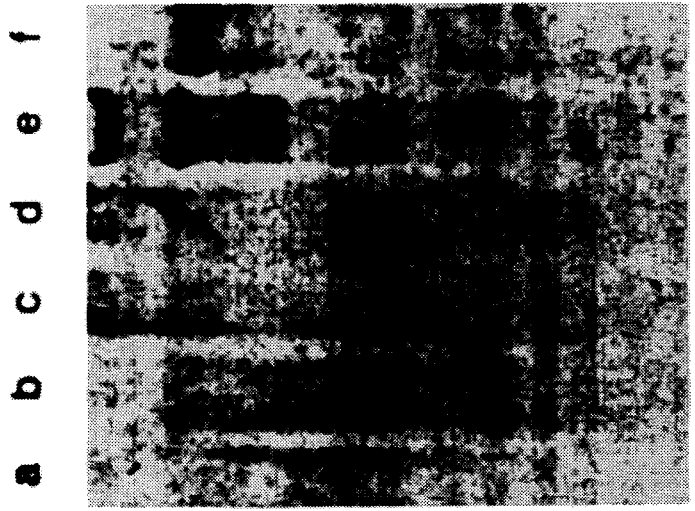
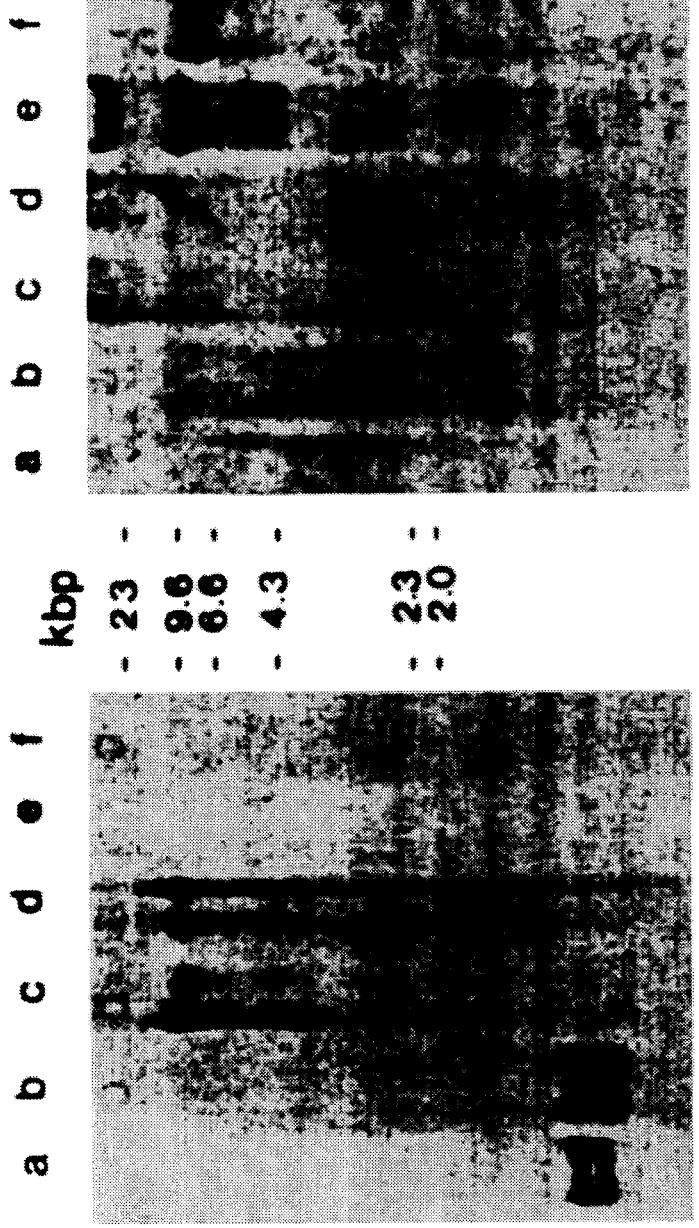

METHODS, KITS, AND PROBES FOR DIAGNOSING HIV-2

This application is a division of U.S. patent application Ser. No. 003,764, filed Jan. 16, 1987, now U.S. Pat. No. 5,051,496, issued Sep. 24, 1991, which is a continuation-in-part of U.S. patent application Ser. No. 06/933,184 of Alizon et al. for "Cloned DNA Sequences Related to the Entire Genomic RNA of Human Immunodeficiency Virus II (HIV-2), Polypeptides Encoded by these DNA Sequences and Use of these DNA Clones and Polypeptides in Diagnostic Kits," filed Nov. 21, 1986, now abandoned in favor of continuation application Ser. No. 604,323, filed Oct. 24, 1990, now abandoned in favor of continuation application Ser. No. 732,748, filed Jul. 18, 1991, abandoned, which is a continuation-in-part application of U.S. patent application Ser. No. 06/916,080 of Montagnier et al, for "Cloned DNA Sequences Related to the Genomic RNA of the Human Immunodeficiency Virus II (HIV-2), Polypeptides Encoded by these DNA Sequences and Use of these DNA Clones and Polypeptide in Diagnostic Kits," filed Oct. 6, 1986, now abandoned in favor of continuation application Ser. No. 602,383, filed Oct. 24, 1990, abandoned, and U.S. patent application Ser. No. 06/835,228 of Montagneir et al, for "New Retrovirus Capable of Causing AIDS, Antigens Obtained from this Retrovirus and Corresponding Antibodies and their Application for Diagnostic Purposes," filed Mar. 3, 1986, now U.S. Pat. No. 4,839,288, issued Jun. 13, 1989.

The invention relates to cloned DNA sequences analogous to the genomic RNA of a virus known as Lymphadenopathy-Associated Virus II ("LAV-II"), a process for the preparation of these cloned DNA sequences, and their use as probes in diagnostic kits. In one embodiment, the invention relates to a cloned DNA sequence analogous to the entire genomic RNA of HIV-2 and its use as a probe. The invention also relates to polypeptides with amino acid sequences encoded by these cloned DNA sequences and the use of these polypeptides in diagnostic kits.

According to recently adopted nomenclature, as reported in Nature, May 1986, a substantially-identical group of retroviruses which has been identified as one causative agent of AIDS are now referred to as Human Immunodeficiency Viruses I (HIV-1). This previously-described group of retroviruses includes Lymphadenopathy-Associated Virus I (LAV-I), Human T-cell Lymphotropic Virus-III (HTLV-III), And AIDS-Related Virus (ARV).

Lymphadenopathy-Associated Virus II has been described in U.S. application Ser. No. 06/835,228, which was filed Mar. 3, 1986, and is specifically incorporated herein by reference. Because LAV-II is a second, distinct causative agent of AIDS, LAV-II properly is classifiable as a Human Immunodeficiency Virus II (HIV-2). Therefore, "LAV-II" as used hereinafter describes a particular genus of HIV-2 isolates.

While HIV-2 is related to HIV-1 by its morphology, its tropism and its in vitro cytopathic effect on CD4 (T4) positive cell lines and lymphocytes, HIV-2 differs from previously described human retroviruses known to be responsible for AIDS. Moreover, the proteins of HIV-1 and 2 have different sizes and their serological cross-reactivity is restricted mostly to the major core protein, as the envelope glycoproteins of HIV-2 are not immune precipitated by HIV-1 positive sera except in some cases where very faint cross-reactivity can be detected. Since a significant proportion of the HIV infected patients lack antibodies to the major core protein of their infecting virus, it is important to include antigens to both HIV-1 and HIV-2 in an effective serum test for the diagnosis of the infection by these viruses.

HIV-2 was first discovered in the course of serological research on patients native to Guinea-Bissau who exhibited clinical and immunological symptoms of AIDS and from whom sero-negative or weakly sero-positive reactions to tests using an HIV-1 lysate were obtained. Further clinical studies on these patients isolated viruses which were subsequently named "LAV-II."

One LAV-II isolate, subsequently referred to as LAV-II MIR, was deposited at the Collection Nationale des Cultures de Micro-Organismes (CNCM) at the Institut Pasteur in Paris, France on Dec. 19, 1985 under Accession No. I-502 and has also been deposited at the British ECA CC under No. 87.001.001 on Jan. 9, 1987. A second LAV-II isolate was deposited at CNCM on Feb. 21, 1986 under Accession No. I-532 and has also been deposited at the British ECA CC under No. 87.001.002 on Jan. 9, 1987. This second isolate has been subsequently referred to as LAV-II ROD. Other isolates deposited at the CNCM on Dec. 19, 1986 are HIV-2 IRMO (No. I-642) and HIV-2 EHO (No. I-643). Several additional isolates have been obtained from West African patients, some of whom have AIDS, others with AIDS-related conditions and others with no AIDS symptoms. All of these viruses have been isolated on normal human lymphocyte cultures and some of them were thereafter propagated on lymphoid tumor cell lines such as CEM and MOLT.

Due to the sero-negative or weak sero-positive results obtained when using kits designed to identify HIV-1 infections in the diagnosis of these new patients with HIV-2 disease, it has been necessary to devise a new diagnositc kit capable of detecting HIV-2 infection, either by itself or in combination with an HIV-1 infection. The present inventors have, through the development of cloned DNA sequences analogous to at least a portion of the genomic RNA of LAV-II ROD viruses, created the materials necessary for the development of such kits.

SUMMARY OF THE INVENTION

As noted previously, the present invention relates to the cloned nucleotide sequences homologous or identical to at least a portion of the genomic RNA of HIV-2 viruses and to polypeptides encoded by the same. The present invention also relates to kits capable of diagnosing an HIV-2 infection.

Thus, a main object of the present invention is to provide a kit capable of diagnosing an infection caused by the HIV-2 virus. This kit may operate by detecting at least a portion of the RNA genome of the HIV-2 virus or the provirus present in the infected cells through hybridization with a DNA probe or it may operate through the immunodiagnostic detection of polypeptides unique to the HIV-2 virus.

Additional objects and advantages of the present invention will be set forth in part in the description which follows, or may be learned from practice of the invention. The objects and advantages may be realized and attained by means of the instrumentalities and combinations particularly pointed out in the appended claims.

To achieve these objects and in accordance with the purposes of the present invention, cloned DNA sequences related to the entire genomic RNA of the LAV-II virus are set forth. These sequences are analogous specifically to the entire genome of the LAV-II ROD strain.

To further achieve the objects and in accordance with the purposes of the present invention, a kit capable of diagnosing an HIV-2 infection is described. This kit, in one embodiment, contains the cloned DNA sequences of this invention which are capable of hybridizing to viral RNA or analogous DNA sequences to indicate the presence of an HIV-2 infection. Different diagnositc techniques can be used which include, but are not limited to: (1) Southern blot procedures to identify cellular DNA which may or may not be digested with restriction enzymes; (2) Northern blot techniques to identify RNA extracted from cells; and (3) dot blot techniques, i.e., direct filtration of the sample through an ad hoc membrane such as nitrocellulose or nylon without previous separation on agarose gel. Suitable material for dot blot technique could be obtained from body fluids including, but not limited to, serum and plasma, supernatants from culture cells, or cytoplasmic extracts obtained after cell lysis and removal of membranes and nuclei of the cells by centrifugation as accomplished in the "CYTODOT" procedure as described in a booklet published by Schleicher and Schull.

In an alternate embodiment, the kit contains the polypeptides created using these cloned DNA sequences. These polypeptides are capable of reacting with antibodies to the HIV-2 virus present in sera of infected individuals, thus yielding an immunodiagnostic complex.

It is understood that both the foregoing general description and the following detailed description are exemplary and explanatory only and are not restrictive of the invention as claimed. The accompanying drawings, which are incorporated in and constituted a part of the specification, illustrate one embodiment of the invention and, together with the description, serve to explain the principles of the invention.

BRIEF DESCRIPTION OF THE DRAWINGS

FIGS. 1A and 1B generally depict the nucleotide sequence of a cloned complementary DNA (cDNA) to the genomic RNA of HIV-2. FIG. 1A depicts the genetic organization of HIV-1, position of the HIV-1 HindIII fragment used as a probe to screen the cDNA library, and restriction map of the HIV-2 cDNA clone, E2. FIG. 1B depicts the nucleotide sequence of the 3' end of the 3' LTR of HIV-2. The corresponding region of the HIV-1 LTR was aligned using the Wilbur and Lipman algorithm (window: 10; K-tuple: 7; gap penalty: 3) as described by Wilbur and Lipman in Proc. Natl. Acad. Sci. USA 80: 726–730 (1983), specifically incorporated herein by reference. The U3-R junction in HIV-1 is indicated and the poly A addition signal and potential TATA promoter regions are boxed. In FIG. 1A, the symbols B, H, Ps and Pv refer to the restriction sites BamHI, HindIII, PstI and PvuII, respectively.

FIGS. 2A–2D generally depict the HIV-2 specificity of the E2 clone. FIGS. 2A and B are line drawings representing Southern Blots of DNA extracted from CEM cells infected with the following isolates: HIV-b $2_{ROD}$ (a,c) HIV-$2_{DUL}$ (b,d) and HIV-$1_{BRU}$ (e,f). Blots a,b,f are PstI digested. Blots c,d,e are undigested. FIGS. 2C and D are line drawings representing dot blot hybridization of pelleted virions from CEM cells infected by the HIV-$_{BRU}$ (1), Simian Immunodeficiency Virus (SIV) isolate Mm 142–83 (3), HIV-$2_{DUL}$ (4), HIV-$2_{ROD}$ (5), and HIV-$1_{ELI}$ (6). Dot 2 is a pellet from an equivalent volume of supernatant from uninfected CEM. Thus, FIGS. 2A and C depicts hybridization with the HIV-2 cDNA (E2) and FIGS. 2B and D depicts hybridization to an HIV-1 probe consisting of a 9.2 kb SacI insert from HIV-$1_{BRU}$.

FIG. 3A specifically depicts the organization of three recombinant phage lambda clones, ROD 4, ROD 27, and ROD35. In FIG. 3A, the open boxes represent viral sequences, the LTR are filled, and the dotted boxes represent cellular flanking sequences (not mapped). Only some characteristic restriction enzyme sites are indicated. λROD 27 and λ35 are derived from integrated proviruses while λROD 4 is derived from a circular viral DNA. The portion of the lambda clones that hybridzes to the cDNA E2 is indicated below the maps. A restriction map of the λROD isolate was reconstructed from these three lambda clones. In this map, the restriction sites are identified as follows: B: BamHI; E: EcoRI; H: HindIII; K: KpnI; Ps: PstI; Pv: PvuII; S: SacI; X: XbaI. R and L are the right and left BamHI arms of the lambda L47.1 vector.

FIG. 3B specifically depicts dots 1–11 which correspond to the single-stranded DNA form of M13 subclones from the HIV-$1_{BRU}$ cloned genome. Their size and position on the HIV-1 genome, determined by sequencing is shown below the figure. Dot 12 is a control containing lambda phage DNA. The dot-blot was hybridized in low stringency conditions as described in Example 1 with the complete lambda λROD 4 clone as a probe, and successively washed in 2×SSC, 0.1% SDS at 25° C. (Tm −42° C.), 1×SSC, 0.1% SDS at 60° C. (Tm −20° C.), and 0.1×SSC, 0.1% SDS at 60° C. (Tm −3° C.) and exposed overnight. A duplicate dot blot was hybridized and washed in stringent conditions (as described in Example 2) with the labelled lambda J19 clone carrying the complete HIV-$1_{BRI}$ genome. HIV-1 and HIV-2 probes were labelled the same specific activity ($10^8$ cpm/g.).

FIG. 4A is a line drawing depicting DNA (20 μg, per lane) from CEM cells infected by the isolate HIV-$2_{DUL}$ (panel 1) or peripheral blood lymphocytes (PBL) infected by the isolates HIV-$2_{GOM}$ (panel 2) and HIV-$2_{MIR}$ (panel 3) digested with: EcoRI (a), PstI b), and HindIII (c). Much less viral DNA was obtained with HIV-2 isolates propagated on PBL. Hybridization and washing were in stringent conditions, as described in Example 2, with $10^6$ cpm/ml. of each of the E2 insert (cDNA) and the 5 kb. HindIII fragment of λROD 4, labelled to $10^9$ cpm/μg.

FIG. 4B is a line drawing depicting DNA from HUT 78 (a human T lymphoid cell line) cells infected with SIV Mm 142–83. The same amounts of DNA and enzymes were used as indicated in panel A. Hybridization was performed with the same probe as in A, but in non-stringent conditions. As described in Example 1 washing was for one hour in 2×SSC, 0.1% SDS at 40° C. (panel 1) and after exposure, the same filter was re-washed in 0.1×SSC, 0.1% SDS at 60° C. (panel 2). The autoradiographs were obtained after overnight exposition with intensifying screens.

DETAILED DESCRIPTION OF THE PREFERRED EMBODIMENTS

Reference will now be made in detail to the presently preferred embodiments of the invention, which, together with the following examples, serve to explain the principles of the invention.

Figure 4B:
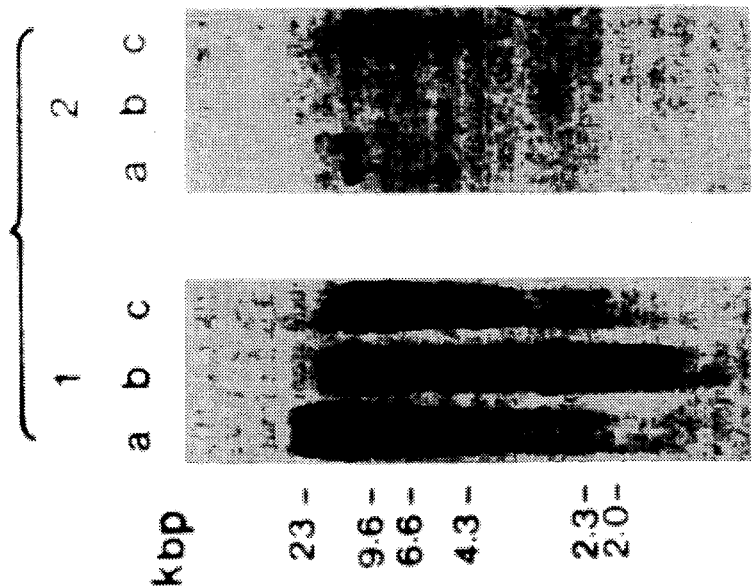
FIGS. 4A and 4B generally depict the restriction map polymorphism in different HIV-2 isolates and shows comparison of HIV-2 to SIV.

The genetic structure of the HIV-2 virus has been analyzed by molecular cloning according to the method set forth herein and in the Examples. A restriction map of the genome of this virus is included in FIG. 4. In addition, the partial sequence of a cDNA complementary to the genomic RNA of the virus has been determined. This cDNA sequence information is included in FIG. 1.

Also contained herein is data describing the molecular cloning of the complete 9.5 kb genome of HIV-2, data describing the observation of restriction map polymorphism between different isolates, and an analysis of the relationship between HIV-2 and other human and simian retroviruses. From the totality of these data, diagnostic probes can be discerned and prepared.

Generally, to practice one embodiment of the present invention, a series of filter hybridizations of the HIV-2 RNA genome with probes derived from the complete cloned HIV-1 genome and from the gag and pol genes were conducted. These hybridizations yielded only extremely weak signals even in conditions of very low stringency of hybridization and washing. Thus, it was found to be difficult to assess the amount of HIV-2 viral and proviral DNA in infected cells by Southern blot techniques.

Therefore, a complementary DNA (cDNA) to the HIV-2 genomic RNA initially was cloned in order to provide a specific hybridization probe. To construct this cDNA, an oligo (dT) primed cDNA first-strand was made in a detergent-activated endogenous reaction using HIV-2 reverse transciptase with virions purified from supernatants of infected CEM cells. The CEM cell line is a lymphoblastoid CD4+ cell line described by G. E Foley et al. in Cancer 18: 522–529 (1965), specifically incorporated herein by reference. The CEM cells used were infected with the isolate ROD and were continuously producing high amounts of HIV-2.

After second-strand synthesis, the cDNAs were inserted into the TG130 M13 bacteria phage vector. A collection of $10^4$ M13 recombinant phages was obtained and screened in situ with an HIV-1 probe spanning 1.5 kb. of the 3' end of the $LAV_{BRU}$ isolate (depicted in FIG. 1A). Some 50 positive plagues were detected, purified, and characterized by end sequencing and cross-hybridizing the inserts. This procedure is described in more detail in Example 1 and in FIG. 1.

The different clones were found to be complementary to the 3' end of a polyadenylated RNA having the AATAAA signal about 20 nucleotides upstream of the poly A tail, as found in the long terminal repeat (LTR) of HIV-1. The LTR region of HIV-1 has been described by S. Wain Hobson et al. in Cell 40: 9–17 (1985), specifically incorporated herein by reference. The portion of the HIV-2 LTR that was sequenced was related only distantly to the homologour domain in HIV-1 as demonstrated in FIG. 1B. Indeed, only about 50% of the nucleotides could be aligned and about a hundred insertions/deletions need to be introduced. In comparison, the homology of the corresponding domains in HIV-1 isolates from USA and Africa is greater than 95% and no insertions or deletions are seen.

Figure 4A:
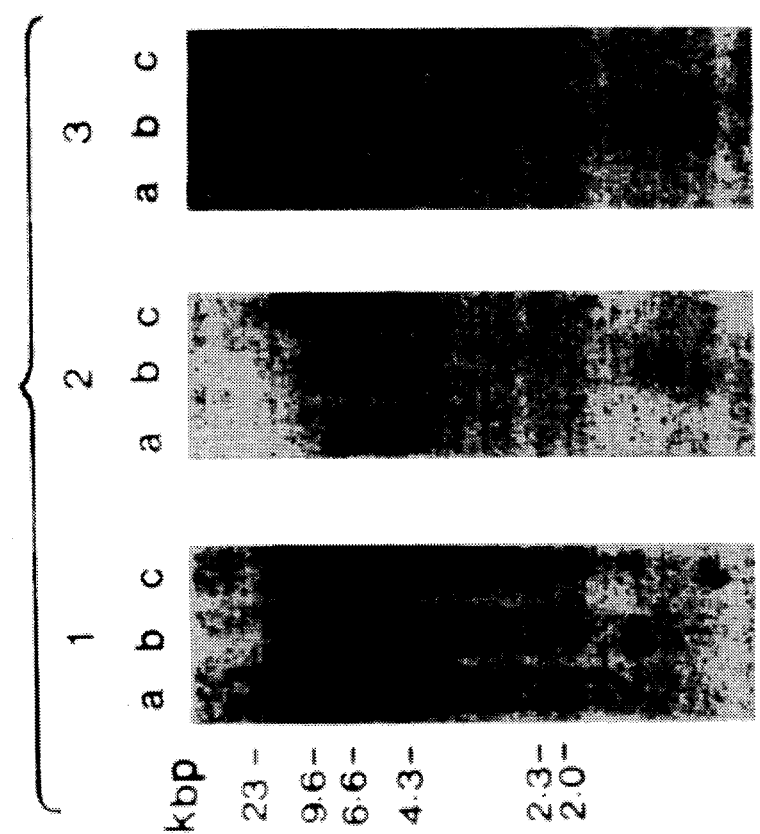

The largest insert of this group of M13 clones was a 2 kb. clone designated E2. Clone E2 was used as a probe to demonstrate its HIV-2 specificity in a series of filter hybridization experiments. Firstly, this probe could detect the genomic RNA of HIV-2 but not HIV-1 in stringent conditions as shown in FIGS. 2C and D. Secondly, positive signals were detected in Southern blots of DNA from cells infected with the ROD isolate as well as other isolates of HIV-2 as shown in FIG. 2A and FIG 4A. No signal was detected with DNA from uninfected cells or HIV-1 infected cells, confirming the exogenous nature of HIV-2. In undigested DNA from HIV-2 infected cells, an approximately 10 kb. species, probably corresponding to linear unintegrated viral DNA, was principally detected along with a species with an apparent size of 6 kb., likely to be the circular form of the viral DNA. Conversely, rehybridization of the same filter with an HIV-1 probe under stringent conditions showed hybridization to HIV-1 infected cells only as depicted in FIG. 2B.

To isolate the remainder of the genome of HIV-2, a genomic library in lambda phage L47.1 was constructed. Lambda phage L47.1 has been described by W. A. M Loenen et al. in Gene 10: 249–259 (1980), specifically incorporated herein by reference. The genomic library was constructed with a partial Sau3AI restriction digest of the DNA from the CEM cell line infected with HIV-$2_{ROD}$.

About $2 \times 10^6$ recombinant plaques were screened in situ with labelled insert from the E2 cDNA clone. Ten recombinant phages were detected and plaque purified. Of these phages, three were characterized by restriction mapping and Southern blot hybridization with the E2 insert and probes from its 3' end (LTR) or 5' end (envelope), as well as with HIV-1 subgenomic probes. In this instance, HIV-1 probes were used under non-stringent conditions.

Figure 3A:
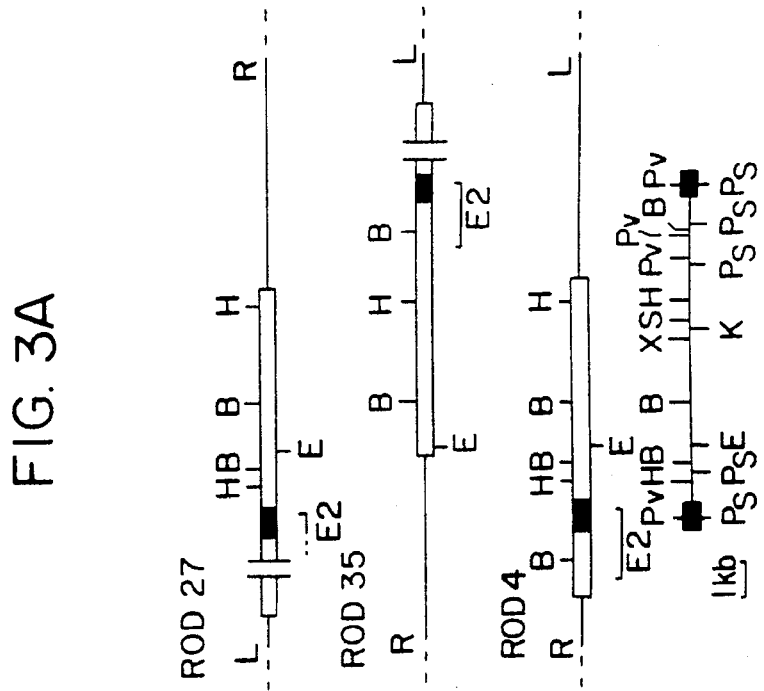
FIGS. 3A and 3B generally depict a restriction map of the HIV-2 ROD genome and its homology to HIV-1.

A clone carrying a 9.5 kb. insert and derived from a circular viral DNA was identified as containing the complete genome and designated λROD 4. Two other clones, λROD 27 and λROD 35 were derived from integrated proviruses and found to carry an LTR and cellular flanking sequences and a portion of the viral coding sequences as shown in FIG. 3A.

Fragments of the lambda clones were subcloned into a plasmid vector p UC 18.

Plasmid pROD 27-5' is derived from λROD 27 and contains the 5'2 kb of the HIV-2 genome and cellular flanking sequences (5' LTR and 5' viral coding sequences to the EcoRI site).

Plasmid pROD 4.8 is derived from λROD 4 and contains the about 5 kb HindIII fragments that is the central part of the HIV-2 genome.

Plasmid pROD 27-5' and p ROD 4.8 inserts overlap.

Plasmid pROD 4.7 contains a HindIII 1.8 kb fragment from λROD 4. This fragment is located 3' to the fragment subcloned into pROD 4.8 and contains about 0.8 kb of viral coding sequences and the part of the lambda phage (λL47.1) left arm located between the BamHI and HindIII cloning sites.

Plasmid pROD 35 contains all the HIV-2 coding sequences 3' to the EcoRI site, the 3' LTR and about 4 kb of cellular flanking sequences.

Figure 5:
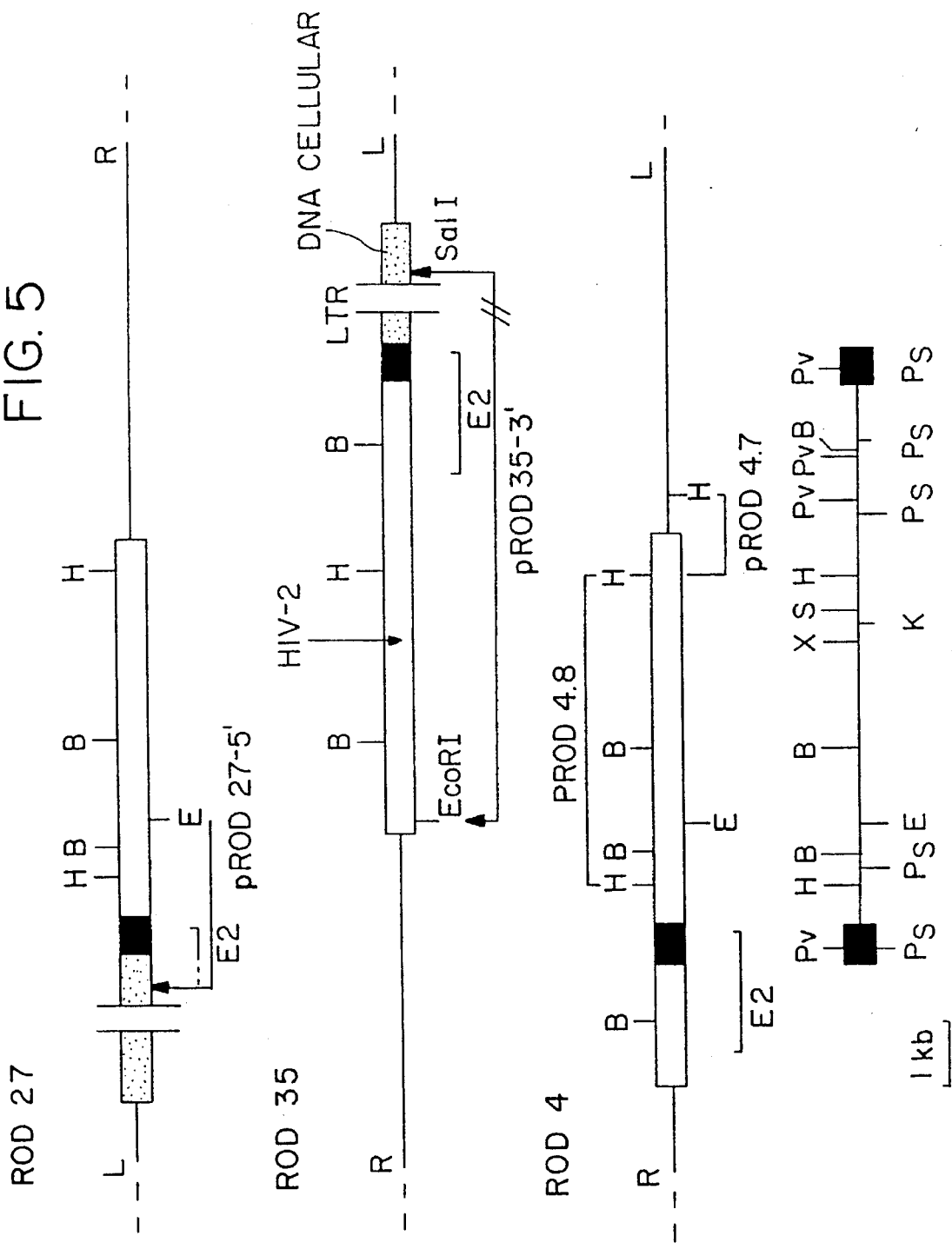
FIG. 5 depicts plasmids λROD 27, λROD 35 and λROD 4.

Plasmid pROD 27-5' and pROD 35 in E. coli strain HB 101 are deposited respectively under No. 1-626 and 1-633 at the CNCM, and have also been deposited at the NCIB (British Collection). These plasmids are depicted in FIG. 5. Plasmid pROD 4.7 and pROD 4.8 in E. coli strain TG1 are deposited respectively under No. 1-627 and 1-628 at the CNCM.

To reconstitute the complete HIV-2 ROD genome, pROD 35 is linearized with EcoRI and the EcoRI insert of pROD 27-5' is ligated in the correct orientation into this site.

Figure 3B:
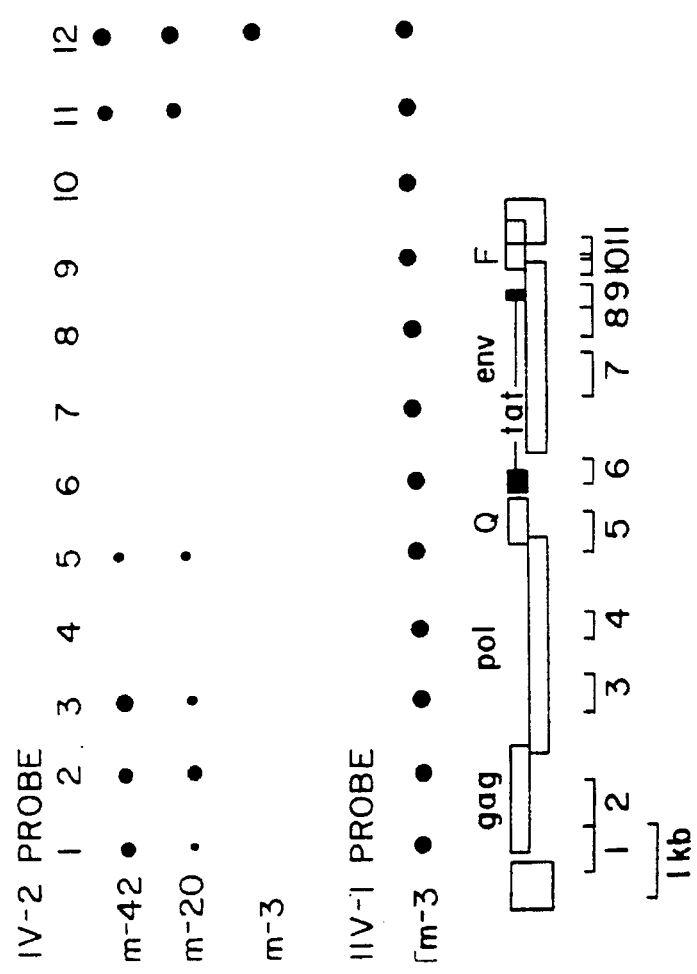

The relationship of HIV-2 to other human and simian retroviruses was surmised from hybridization experiments. The relative homology of the different regions of the HIV-1 and 2 genomes was determined by hybridization of fragments of the cloned HIV-1 genome with the labelled λROD 4 expected to contain the complete HIV-2 genome (FIG. 3B). Even in very low stringency conditions (Tm-42° C.), the hybridization of HIV-1 and 2 was restricted to a fraction of their genomes, principally the gag gene (dots 1 and 2), the reverse transcriptase domain in pol (dot 3), the end of pol and the Q (or sor) genes (dot 5) and the F gene (or 3' orf) and 3' LTR (dot 11). The HIV-1 fragment used to detect the HIV-2 cDNA clones contained the dot 11 subclone, which hybridized well to HIV-2 under non-stringent conditions. Only the signal from dot 5 persisted after stringent washing. The envelope gene, the region of the tat gene and a part of pol thus seemed very divergent. These data, along with the LTR sequence obtained (FIG. 1B), indicated that HIV-2 is not an envelope variant of HIV-1 as described by Alizon et al., *Cell* 40: 63–74 (1986).

It was observed that HIV-2 is related more closely to the Simian Immunodeficiency Virus (SIV) than it is to HIV-1. This correlation has been described by F. Clavel et al. in C.R. Acad. Sci. (Paris) 302: 485–488 (1986) and F. Clavel et al. in Science 233: 343–346 (1986), both of which are specifically incorporated herein by reference. Simian Immunodeficiency Virus (also designated Simian T-cell Lymphotoropic Virus Type 3, STLV-3) is a retrovirus first isolated from captive macaques with an AIDS-like disease in the USA. This simian virus has been described by M. D. Daniel et al. in Science 228: 1201–1204 (1985), specifically incorporated herein by reference.

All the SIV proteins, including the envelope, are immune precipitated by sera from HIV-2 infected patients, whereas the serological cross-reactivity of HIV-1 and 2 is restricted to the core proteins. However SIV and HIV-2 can be distinguished by slight differences in the apparent molecular weight of their proteins.

In terms of nucleotide sequence, it also appears that HIV-2 is closely related to SIV. The genomic RNA of SIV can be detected in stringent conditions as shown in FIG. 2C by HIV-2 probes corresponding to the LTR and 3' end of the genome (E2) or to the gag or pol genes. Under the same conditions, HIV-1 derived probes do not detect the SIV genome as shown in FIG. 2D.

In Southern blots of DNA from SIV-infected cells, a restriction pattern clearly different from HIV-2$_{ROD}$ and other isolates is seen. All the blends persist after a stringent washing, even though the signal is considerably weakened, indicating a sequence homology throughout the genomes of HIV-2 and SIV. It has recently been shown that baboons and macaques could be infected experimentally by HIV-2, thereby providing an interesting animal model for the study of the HIV infection and its preventive therapy. Indeed, attempts to infect non-human primates with HIV-1 have been successful only in chimpanzees, which are not a convenient model.

From an initial survey of the restriction maps for certain of the HIV-2 isolates obtained according to the methods described herein, it is already apparent that HIV-2, like HIV-1, undergoes restriction site polymorphism. FIG. 4A depicts examples of such differences for three isolates, all different one from another and from the cloned HIV-2$_{ROD}$. It is very likely that these differences at the nucleotide level are accompanied by variations in the amino-acid sequence of the viral proteins, as evidenced in the case of HIV-1 and described by M. Alizon et al. in Cell 46: 63–74 (1986), specifically incorporated herein by reference. It is also to be expected that the various isolates of HIV-2 will exhibit other minor amino acid heterogeneities. See, for example, Clavel et al., *Nature* 324 (18): 691–695 (1986), specifically incorporated herein by reference.

Further, the characterization of HIV-2 will also delineate the domain of the envelope glycoprotein that is responsible for the binding of the surface of the target cells and the subsequent internalization of the virus. This interaction was shown to be mediated by the CD4 molecule itself in the case of HIV-1 and similar studies tend to indicate that HIV-2 uses the same receptor. Thus, although there is wide divergence between the env genes of HIV-1 and 2, small homologous domains of the envelopes of the two HIV could represent a candidate receptor binding site. This site could constitute a target for use to raise a protective immune response against this group of retroviruses.

From the data discussed herein, certain nucleotide sequences have been identified which are capable of being used as probes in diagnostic methods to obtain the immunological reagents necessary to diagnose an HIV-2 infection. In particular, these sequences may be used as probes in hybridization reactions with the genetic material of infected patients to indicate whether the RNA of the HIV-2 virus is present in these patient's lymphocytes or whether an analogous DNA is present. In this embodiment, the test methods which may be utilized include Northern blots, Southern blots and dot blots. One particular nucleotide sequence which may be useful as a probe is the combination of the 5 kb. HindIII fragment of ROD 4 and the E2 cDNA used in FIG. 4.

In addition, the genetic sequences of the HIV-2 virus may be used to create the polypeptides uncoded by these sequences. Specifically, these polypeptides may be created by expressions of the cDNA obtained according to the teachings herein in hosts such as bacteria, yeast or animal cells. These polypeptides may be used in diagnostic tests such as immunofluoroescence assays (IFA), radioimmunoassays (RIA) and Western Blot tests.

Moreover, it is also contemplated that additional diagnostic tests, including additional immunodiagnostic tests, may be developed in which the DNA probes or the polypeptides of this invention may serve as one of the diagnostic reagents. The invention described herein includes these additional test methods.

In addition, monoclonal antibodies to these polypeptides or fragments thereof may be created. The monoclonal antibodies may be used in immunodiagnostic tests in an analogous manner as the polypeptides described above.

The polypeptides of the present invention may also be used as immunogenic reagents to induce protection against infection by HIV-2 viruses. In this embodiment, the polypeptides produced by recombinant-DNA techniques would function as vaccine agents.

Also, the polypeptides of this invention may be used in competitive assays to test the ability of various antiviral agents to determine their ability to prevent the virus from fixing on its target.

Thus, it is to be understood that application of the teachings of the present invention to a specific problem or environment will be within the capabilities of one having ordinary skill in the art in light of the teachings contained herein. Examples of the products of the present invention and representative processes for their isolation and manufacture appear above and in the following examples.

EXAMPLES

EXAMPLE 1

Cloning of a cDNA Complementary to Genomic RNA From HIV-2 Virions

HIV-2 virions were purified from 5 liters of supernatant from a culture of the CEM cell line infected with the ROD isolate and a cDNA first strand using oligo (dT) primer was synthesized in detergent activated endogenous reaction on pelleted virus, as described by M. Alizon et al. in Nature, 312: 757–760 (1984), specifically incorporated herein by reference. RNA-cDNA hybrids were purified by phenol-chloroform extraction and ethanol precipitation. The second-strand cDNA was created by the DNA polymerase I/RNAase H method of Sanger et al. described in Proc. Nat'l Acad. Sci. USA, 74: 5463–5467 (1977), specifically incorporated herein by reference. The double-stranded cDNA was blunt-ended with T4 DNA polymerase using a commercial cDNA synthesis kit (obtained from Amersham). After attachment of EcoRI linkers (obtained from Pharmacia), EcoRI digestion, and ligation into Eco-RI-digested dephosphorylated M13 tg 130 vector (obtained from Amersham), a cDNA library was obtained by transformation of the *E. coli* TGl strain. Recombinant plaques ($10^4$) were screened in situ on replica filters with the 1.5 kb. HindIII fragment from clone J19, corresponding to the 3' part of the genome of the $LAV_{BRU}$ isolate of HIV-1, $^{32}P$ labelled to a specific activity of $10^9$ cpm/μg. The filters were prehybridized in 5×SSC, 5×Denhardt solution, 25% formamide, and denatured salmon sperm DNA (100 μg/ml.) at 37° C. for 4 hours and hybridized for 16 hours in the same buffer (Tm −42° C.) plus $4×10^7$ cpm of the labelled probe ($10^6$ cpm/ml. of hybridization buffer). The washing was done in 5×SSC, 0.1% SDS at 25° C. for 2 hours. 20×SSC is 3M NaCl, 0.3M Na citrate. Positive plaques were purified and single-stranded M13 DNA prepared and end-sequenced according to the method of Sanger et al., supra.

EXAMPLE 2

Hybridization of DNA from HIV-1 and HIV-2 Infected Cells and RNA from HIV-1 and 2 and SIV Virons With a Probe Derived From an HIV-2 Cloned cDNA DNA was extracted from infected CEM cells continuously producing HIV-1 or 2. The DNA digested with 20 μg of PstI or undigested, was electrophoresed on a 0.8% agarose gel, and Southern-transferred to nylon membrane. Virion dot-blots were prepared in duplicate, as described by F. Clavel et al. in Science 233: 343–346 (1986), specifically incorporated herein by reference, by pelleting volumes of supernatant corresponding to the same amount of reverse transcriptase activity. Prehybridization was done in 50% formamide, 5×SSC, 5×Denhardt solution, and 100 mg./ml. denatured salmon sperm DNA for 4 hours at 42° C. Hybridization was performed in the same buffer plus 10% Dextran sulphate, and $10^6$ cpm/ml. of the labelled E2 insert (specific activity $10^9$ cpm/μg.) for 16 hours at 42° C. Washing was in 0.1×SSC, 0.1% SDS for 2×30 min. After exposure for 16 hours with intensifying screens, the Southern blot was dehybridized in 0.4N NaOH, neutralized, and rehybridized in the same conditions to the HIV-1 probe labelled to $10^9$ cpm/μg.

EXAMPLE 3

Cloning in Lambda Phage of the Complete Provirus DNA of HIV-2

DNA from the HIV-$2_{ROD}$ infected CEM (FIG. 2, lanes a and c) was partially digested with Sau3AI. The 9–15 kb. fraction was selected on a 5–40% sucrose gradient and ligated to BamHI arms of the lambda L47.1 vector. Plaques ($2×10^6$) obtained after in vitro packaging and plating on *E. coli* LA 101 strain were screened in situ with the insert from the E2 cDNA clone. Approximately 10 positive clones were plaque purified and propagated on *E. coli* C600 recBC. The ROD 4, 27, and 35 clones were amplified and their DNA characterized by restriction mapping and Southern blotting with the HIV-2 cDNA clone under stringent conditions, and gag-pol probes from HIV-1 used under non stringent conditions.

EXAMPLE 4

Sequences of the Coding Regions for the Envelope Protein and GAG Product of the ROD HIV-2 Isolate Additional experimental analysis of the HIV-2 ROD isolate was performed and has yielded the following sequences for the env and gag sequences. Regions coding for amino acid sequences corresponding to known proteins characterized by apparent molecular weights have been identified within the gag sequence: p. 16 (nucleotides 1-405), p. 26 (406–1155) and p. 12 (1156–1566).

Envelope sequence:

Met Met Asn Gln Leu Leu Ile Ala Ile Leu Leu Ala Ser Ala Cys
ATGATGAATCAGCTGCTTATTGCCATTTTATTAGCTAGTGCTTGC

Leu Val Tyr Cys Thr Gln Tyr Val Thr Val Phe Tyr Gly Val Pro
TTAGTATATTGCACCCAATATGTAACTGTTTTCTATGGCGTACCC

Thr Trp Lys Asn Ala Thr Ile Pro Leu Phe Cys Ala Thr Arg Asn
ACGTGGAAAAATGCAACCATTCCCCTGTTTTGTGCAACCAGAAAT
100

Arg Asp Thr Trp Gly Thr Ile Gln Cys Leu Pro Asp Asn Asp Asp
AGGGATACTTGGGGAACCATACAGTGGTTGCCTGACAATGATGAT

Tyr Gln Glu Ile Thr Leu Asn Val Thr Glu Ala Phe Asp Ala Trp
TATCAGGAAATAACTTTGAATGTAACAGAGGCTTTTGATGCATGG
200

Asn Asn Thr Val Thr Glu Gln Ala Ile Glu Asp Val Trp His Leu
AATAATACAGTAACAGAACAAGCAATAGAAGATGTCTGGCATCTA

-continued

```
Phe Glu Thr Ser Ile  Lys Pro Cys Val Lys Leu Thr Pro Leu Cys
TTCGAGACATCAATAAAACCATGTGTGAAACTAACACCTTTATGT
         •           •           300           •

Val Ala Met Lys Cys Ser Ser Thr Glu Ser Ser Thr Gly Asn Asn
GTAGCAATGAAATGCAGCAGCACAGAGAGCAGCACAGGGAACAAC
         •        •        •         •        •

Thr Thr Ser Lys Ser Thr Ser Thr Thr Thr Thr Thr Pro Thr Asp
ACAACCTCAAAGAGCACAAGCACAACCACAACCACACCCAGAGAC
         •        •        •         400

Gln Glu Gln Glu Ile  Ser Glu Asp Thr Pro Cys Als Arg Ala Asp
CAGGAGCAAGAGATAAGTGAGGATACTCCATGGGGACGCGCAGAC
         •        •        •         •        •

Asn Cys Ser Gly Leu Gly Glu Glu Glu Thr Ile  Asn Cys Gln Phe
AACTGCTCAGGATTGGGAGAGGAAGAAACGATCAATTGCCAGTTC
         •        •        •         •

Asn Met Thr Gly Leu Glu Arg Asp Lys Lys Lys Gln Tys Asn Glu
AATATGACAGGATTAGAAAGAGATAAGAAAAAACAGTATAATGAA
       500        •        •         •        •

Thr Trp Tyr Ser Lys Asp Val Val Cys Glu Thr Asn Asn Ser Thr
ACATGGTACTCAAAAGATGTGGTTTGTGAGACAAATAATAGCACA
         •        •        •         •

Asn Gln Thr Gln Cys Tyr Met Asn His Cys Asn Thr Ser Val Ile
AATCAGACCCAGTGTTACATGAACCATTGCAACACATCAGTCATC
         •       600        •         •        •

Thr Glu Ser Cys Asp Lys His Tyr Trp Asp Ala Ile  Arg Phe Arg
ACAGAATCATGTGACAAGCACTATTGGGATGCTATAAGGTTTAGA
         •        •        •         •

Tyr Cys Ala Pro Pro Gly Tyr Ala Leu Leu Arg Cys Asn Asp Thr
TACTGTGCACCACCGGGTTATGCCCTATTAAGATGTAATGATACC
         •        •       700        •        •

Asn Tyr Ser Gly Phe Ala Pro Asn Cys Ser Lys Val Val Ala Ser
AATTATTCAGGCTTTGCACCCAACTGTTCTAAAGTAGTAGCTTCT
         •        •        •         •

Thr Cys Thr Arg Met Met Glu Thr Gln Thr Ser Thr Trp Phe Gly
ACATGCACCAGGATGATGGAAACGCAAACTTCCACATGGTTTGGG
         •        •        •        800  •

Phe Asn Gly Thr Arg Ala Glu Asn Arg Thr Tyr Ile  Tyr Trp His
TTTAATGGCACTAGAGCAGAGAATAGAACATATATCTATTGGCAT
         •        •        •         •

Gly Arg Asp Asn Arg Thr Ile  Ile  Ser Leu Asn Lys Tyr Tyr Asn
GGCAGAGATAATAGAACTATCATCAGCTTAAACAAATATTATAAT
         •        •        •         •       900

Leu Ser Leu His Cys Lys Arg Pro Gly Asn Lys Thr Val Lys Gln
CTCAGTTTGCATTGTAAGAGGCCAGGGAATAAGACAGTGAAACAA
         •        •        •         •

Ile  Met Leu Met Ser Gly His Val Phe His Ser His Tyr Gln Pro
ATAATGCTTATGTCAGGACATGTGTTTCACTCCCACTACCAGCCG
         •        •        •         •        •

Ile  Asn Lys Arg Pro Arg Gln Ala Trp Cys Trp Phe Lys Gly Lys
ATCAATAAAAGACCCAGACAAGCATGGTGCTGGTTCAAAGGCAAA
       1000       •        •         •

Trp Lys Asp Ala Met Gln Glu Val Lys Thr Leu Ala Lys His Pro
TGGAAAGACGCCATGCAGGAGGTGAAGACCCTTGCAAAACATCCC
         •        •        •         •        •

Arg Tyr Arg Gly Thr Asn Asp Thr Arg Asn Ile  Ser Phe Ala Ala
AGGTATAGAGGAACCAATGACACAAGGAATATTAGCTTTGCAGCG
         •      1100        •         •

Pro Gly Lys Gly Ser Asp Pro Glu Val Ala Tyr Met Trp Thr Asn
CCAGGAAAAGGCTCAGACCCAGAAGTAGCATACATGTGGACTAAC
         •        •        •         •        •

Cys Arg Gly Glu Phe Leu Tyr Cys Asn Met Thr Trp Phe Leu Asn
TGCAGAGGAGAGTTTCTCTACTGCAACATGACTTGGTTCCTCAAT
         •        •       1200        •
```

```
Trp Ile  Glu Asn Lys Thr His Arg Asn Tyr Ala Pro Cys His Ile
TGGATAGAGAATAAGACACACCGCAATTATGCACCGTGCCATATA

Lys Gln Ile  Ile  Asn Thr Trp His Lys Val Gly Arg Asn Val Tyr
AAGCAAATAATTAACACATGGCATAAGGTAGGGAGAAATGTATAT
                                        1300

Leu Pro Pro Arg Glu Gly Glu Leu Ser Cys Asn Ser Thr Val Thr
TTGCCTCCCAGGGAAGGGGAGCTGTCCTGCAACTCAACAGTAACC

Ser Ile  Ile  Ala Asn Ile  Asp Trp Gln Asn Asn Asn Gln Thr Asn
AGCATAATTGCTAACATTGACTGGCAAAACAATAATCAGACAAAC

Ile  Thr Phe Ser Ala Glu Val Ala Glu Leu Tyr Arg Leu Glu Leu
ATTACCTTTAGTGCAGAGGTGGCAGAACTATACAGATTGGAGTTG
    1400

Gly Asp Tyr Lys Leu Val Glu Ile  Thr Pro Ile  Gly Phe Ala Pro
GCAGATTATAAATTGGTAGAAATAACACCAATTGGCTTCGCACCT

Thr Lys Glu Lys Arg Tyr Ser Ser Ala His Gly Arg His Thr Arg
ACAAAAGAAAAAAGATACTCCTCTGCTCACGGGAGACATAGAAGA
         1500

Gly Val Phe Val Leu Gly Phe Leu Gly Phe Leu Ala Thr Ala Gly
GGTGTGTTCGTGCTAGGGTTCTTGGGTTTTCTCGCAACAGCAGGT

Ser Ala Met Gly Ala Arg Ala Ser Leu Thr Val Ser Ala Gln Ser
TCTGCAATGGGCGCTCGAGCGTCCCTGACCGTGTCGGCTCAGTCC
                        1600

Arg Thr Leu Leu Ala Gly Ile  Val Gln Gln Gln Gln Leu Leu
CGGACTTTACTGGCCGGGATAGTGCAGCAACAGCAACAGCTGTTG

Asp Val Val Lys Arg Gln Gln Glu Leu Leu Arg Leu Thr Val Trp
GACGTGGTCAAGAGACAACAAGAACTGTTGCGACTGACCGTCTGG
                              1700

Gly Thr Lys Asn Leu Gln Ala Arg Val Thr Ala Ile  Glu Lys Tyr
GGAACGAAAAACCTCCAGGCAAGAGTCACTGCTATAGAGAAGTAG

Leu Gln Asp Gln Ala Arg Leu Asn Ser Trp Gly Cys Ala Phe Arg
CTACAGGACCAGGCGCGGCTAAATTCATGGGGATGTGCGTTTAGA
                                           1800

Gln Val Cys His Thr Thr Val Pro Trp Val Asn Asp Ser Leu Ala
CAAGTCTGCCACACTACTGTACCATGGGTTAATGATTCCTTAGCA

Pro Asp Trp Asp Asn Met Thr Trp Gln Glu Trp Glu Lys Gln Val
CCTGACTGGGACAATATGACGTGGCAGGAATGGGAAAAACAAGTC

Arg Tyr Leu Glu Ala Asn Ile  Ser Lys Ser Leu Glu Gln Ala Gln
CGCTACCTGGAGGCAAATATCAGTAAAAGTTTAGAACAGGCACAA
      1900

Ile  Gln Gln Glu Lys Asn Met Tyr Glu Leu Gln Lys Leu Asn Ser
ATTCAGCAAGAGAAAAATATGTATGAACTACAAAAATTAAATAGC

Trp Asp Ile  Phe Gly Asn Trp Phe Asp Leu Thr Ser Trp Val Lys
TGGGATATTTTTGGCAATTGGTTTGACTTAACCTCCTGGGTCAAG
                 2000

Tyr Ile  Gln Tyr Gly Val Leu Ile  Ile  Val Ala Val Ile  Ala Leu
TATATTCAATATGGAGTGCTTATAATAGTAGCAGTAATAGCTTTA

Arg Ile  Val Ile  Tyr Val Val Gln Met Leu Ser Arg Leu Arg Lys
AGAATAGTGATATATGTAGTACAAATGTTAAGTAGCCTTAGAAAG
                   2100
```

-continued

Gly Tyr Arg Pro Val Phe Ser Ser Pro Pro Gly Tyr Ile Gln \*\*\*
GGCTATAGGCCTGTTTTCTCTTCCCCCCCCGGTTATATCCAATAG

Ile His Ile His Lys Asp Arg Gly Gln Pro Ala Asn Glu Glu Thr
ATCCATATCCACAAGGACCGGGGACAGCCAGCCAACGAAGAAACA
                                      2200

Glu Glu Asp Gly Gly Ser Asn Gly Gly Asp Arg Tyr Trp Pro Trp
GAAGAAGACGGTGGAAGCAACGGTGGAGACAGATACTGGCCCTGG

Pro Ile Ala Tyr Ile His Phe Leu Ile Arg Gln Leu Ile Arg Leu
GCGATAGCATATACATTTCCTGATCCGCCAGCTGATTCGCCTC

Leu Thr Arg Leu Tyr Ser Ile Cys Arg Asp Leu Leu Ser Arg Ser
TTGACCAGACTATACAGCATCTGCAGGGACTTACTATCCAGGAGC
   2300

Phe Leu Thr Leu Glu Leu Ile Tyr Gln Asn Leu Arg Asp Trp Leu
TTCCTGACCCTCCAACTCATCTACCAGAATCTCAGAGACTGGCTG

Arg Leu Arg Thr Ala Phe Leu Glu Tyr Gly Cys Glu Trp Ile Gln
AGACTTAGAACAGCCTTCTTGCAATATGGGTGCGAGTGGATCCAA
       2400

Glu Ala Phe Gln Ala Ala Ala Arg Ala Thr Arg Glu Thr Leu Ala
GAAGCATTCCAGGCCGCCGCGAGGGCTACAAGAGAGACTCTTGCG

Gly Ala Cys Arg Gly Leu Trp Arg Val Leu Glu Arg Ile Gly Arg
GGCGCGTGCAGGGGCTTGTGGAGGGTATTGGAACGAATCGGGAGG
             2500

Gly Ile Leu Ala Val Pro Arg Arg Ile Arg Gln Gly Ala Glu Ile
GGAATACTCGCGGTTCCAAGAAGGATCAGACAGGGAGCAGAAATC

Ala Leu Leu \*\*\* Gly Thr Ala Val Ser Ala Gly Arg Leu Tyr Glu
GCCCTCCTGTGAGGGACGGCAGTATCAGCAGGGAGACTTTATGAA
                     2600

Tyr Ser Met Glu Gly Pro Ser Ser Arg Lys Gly Glu Lys Phe Val
TACTCCATGGAAGGACCCACCAGCAGAAAGGGAGAAAAATTTGTA

Gln Ala Thr Lys Tyr Gly
GAGGCAACAAAATATGGA

GAG sequence:

Met Gly Ala Arg Asn Ser Val Leu Arg Gly Lys Lys Ala Asp Glu
ATGGGCGCGAGAAACTCCGTCTTGAGAGGGAAAAAAGCAGATGAA

Leu Glu Arg Ile Arg Leu Arg Pro Gly Gly Lys Lys Lys Tyr Arg
TTAGAAAGAATCAGGTTACGGCCCGGCGGAAAGAAAAAGTACAGG

Leu Lys His Ile Val Trp Ala Ala Asn Lys Leu Asp Arg Phe Gly
CTAAAACATATTGTGTGGGCAGCGAATAAATTGGACAGATTCGGA
     100

Leu Ala Glu Ser Leu Leu Glu Ser Lys Glu Glu Cys Gln Lys Ile
TTAGCAGAGAGCCTGTTGGAGTCAAAAGAGGGTTGTCAAAAAATT

Leu Thr Val Leu Asp Pro Met Val Pro Thr Gly Ser Glu Asn Leu
CTTACAGTTTTAGATCCAATGGTACCGACAGGTTCAGAAAATTTA
           200

Lys Ser Leu Phe Asn Thr Val Cys Val Ile Trp Cys Ile His Ala
AAAAGTCTTTTTAATACTGTCTGCGTCATTTGGTGCATACACGCA

Glu Glu Lys Val Lys Asp Thr Glu Gly Ala Lys Gln Ile Val Arg
GAAGAGAAAGTGAAAGATACTGAAGGAGCAAAACAAATAGTGCGG
                 300

```
Arg His Leu Val Ala Glu Thr Gly Thr Ala Glu Lys Met Pro Ser
AGACATCTAGTGGCAGAAACAGGAACTGCAGAGAAAATGCCAACC

Thr Ser Arg Pro Thr Ala Pro Ser Ser Glu Lys Gly Gly Asn Tyr
ACAAGTAGACCAACAGCACCATCTAGCGAGAAGGGAGGAAATTAC
                                       400

Pro Val Gln His Val Gly Gly Asn Tyr Thr His Ile Pro Leu Ser
CCAGTGCAACATGTAGGCGGCAACTACACCCATATACCGCTGAGT

Pro Arg Thr Leu Asn Ala Trp Val Lys Leu Val Glu Glu Lys Lys
CCCCGAACCCTAAATGCCTGGGTAAAATTAGTAGAGGAAAAAAAG

Phe Gly Ala Glu Val Val Pro Gly Phe Gln Ala Leu Ser Glu Gly
TTCGGGGCAGAAGTAGTGCCAGGATTTCAGGCACTCTCAGAAGGC
     500

Cys Thr Pro Tyr Asp Ile Asn Gln Met Leu Asn Cys Val Gly Asp
TGCACGCCCTATGATATCAACCAAATGCTTAATTGTGTGGGCGAC

His Gln Ala Ala Met Gln Ile Ile Arg Glu Ile Ile Asn Glu Glu
CATCAAGCAGCCATGCAGATAATCAGCGAGATTATCAATGAGGAA
          600

Ala Ala Glu Trp Asp Val Gln His Pro Ile Pro Gly Pro Leu Pro
GCAGCAGAATGGGATGTGCAACATCCAATACCAGGCCCCTTACCA

Ala Gly Glu Leu Arg Glu Pro Arg Gly Ser Asp Ile Ala Gly Thr
GCGGGGCAGCTTAGAGAGCCAAGGGGATCTGACATAGCAGGGACA
                    700

Thr Ser Thr Val Glu Glu Gln Ile Gln Trp Met Phe Arg Pro Gln
ACAAGCACAGTAGAAGAACAGATCCAGTGGATGTTTAGGCCACAA

Asn Pro Val Pro Val Gly Asn Ile Tyr Arg Arg Trp Ile Gln Ile
AATCCTGTACCAGTAGGAAACATCTATAGAAGATGGATCCAGATA
                              800

Gly Leu Gln Lys Cys Val Arg Met Tyr Asn Pro Thr Asn Ile Leu
GGATTGCAGAAGTGTGTCAGGATGTACAACCCGACCAACATCCTA

Asp Ile Lys Gln Gly Pro Lys Glu Pro Phe Gln Ser Tyr Val Asp
GACATAAAACAGGGACCAAAGGAGCCGTTCCAAAGCTATGTAGAT
                                            900

Arg Phe Tyr Lys Ser Leu Arg Ala Glu Gln Thr Asp Pro Ala Val
AGATTCTACAAAAGCTTGAGGGCAGAACAAACAGATCCAGCAGTG

Lys Asn Trp Met Thr Gln Thr Leu Leu Val Gln Asn Ala Asn Pro
AAGAATTGGATGACCCAAACACTGCTAGTACAAAATGCCAACCCA

Asp Cys Lys Leu Val Leu Lys Gly Leu Gly Met Asn Pro Thr Leu
GACTGTAAATTAGTGCTAAAAGGACTAGGGATGAACCCTACCTTA
         1000

Glu Glu Met Leu Thr Ala Cys Gln Gly Val Gly Gly Pro Gly Gln
GAAGAGATGCTGACCGCCTGTCAGGGCGTAGGTGGGCCAGGCCAG

Lys Ala Arg Leu Met Ala Glu Ala Leu Lys Glu Val Ile Gly Pro
AAAGCTAGATTAATGGCAGAGGCCCTGAAAGAGGTCATAGGACCT
              1100

Ala Pro Ile Pro Phe Ala Ala Ala Gln Gln Arg Lys Ala Phe Lys
GCCCCTATCCCATTCGCAGCAGCCCAGCAGAGAAAGGCATTTAAA

Cys Trp Asn Cys Gly Lys Glu Gly His Ser Ala Arg Gln Cys Arg
TGCTGGAACTGTGGAAAGGAAGGGCACTCGGCAAGACAATGCCGA
                        1200

Ala Pro Arg Arg Gln Gly Cys Trp Lys Cys Gly Lys Pro Gly His
GCACCTAGAAGGCAGGGCTGCTGGAAGTGTGGTAAGCCAGGACAC
```

```
Ile Met Thr Asn Cys Pro Asp Arg Gln Ala Gly Phe Leu Gly Leu
ATCATGACAAACTGCCCAGATAGACAGGCAGGTTTTTTAGGACTG
                                         1300

Gly Pro Trp Gly Lys Lys Pro Arg Asn Phe Pro Val Ala Gln Val
GGCCCTTGGGGAAAGAAGCCCCGCAACTTCCCCGTGGCCCAAGTT

Pro Gln Gly Leu Thr Pro Thr Ala Pro Pro Val Asp Pro Ala Val
CCGCAGGGGCTGACACCAACAGCACCCCCAGTGGATCCAGCAGTG

Asp Leu Leu Glu Lys Tyr Met Gln Gln Gly Lys Arg Gln Arg Glu
GATCTACTGGAGAAATATATGCAGCAAGGGAAAAGACAGAGAGAG
    1400

Gln Arg Glu Arg Pro Tyr Lys Glu Val Thr Glu Asp Leu Leu His
CAGAGAGAGAGACCATACAAGGAAGTGACAGAGGACTTACTGCAC

Leu Glu Gln Gly Glu Thr Pro Tyr Arg Glu Pro Pro Thr Glu Asp
CTCGAGCAGGGGGAGACACCATACAGGGAGCCACCAACAGAGGAC
              1500

Leu Leu His Leu Asn Ser Leu Phe Gly Lys Asp Gln
TTGCTGCACCTCAATTCTCTCTTTGGAAAAGACCAG
```

EXAMPLE 5

Peptide Sequences Encoded By The ENV and GAG Sequences

The following coding regions for antigenic peptides, identified by nucleotide numbers within the gene sequences of Example 4, are of particular interest.

env1 (1735

```
                                    Thr Trp Lys Asn Ala Thr Ile  Pro Leu Phe Cys Ala Thr
                                    ACGTGGAAAAATGCAACCATTCCCCTGTTTTGTGCAACG
                                              100         •         • env5 (175–231)

Asp Asp
                                                                              GATGAT
                                                                                 •

Tyr Gln Glu Ile  Thr Leu Asn Val Thr Glu Ala Phe Asp Ala Trp
TATCAGGAAATAACTTTGAATGTAACAGAGGCTTTTGATGCATGG
         •                 200        •         •

Asn Asn
AATAAT env6 (274–330)

Glu Thr Ser Ile  Lys Pro Cys Val Lys Leu Thr Pro Leu Cys
    GAGACATCAATAAAACCATGTGTGAAACTAACACCTTTATGT
           •           •          300         •

Val Ala Met Lys Cys
GTAGCAATGAAATGC
      •          • env7 (607–660)

Asn His Cys Asn Thr Ser Val Ile
                                AACCATTGCAACACATCAGTCATC
                                   610        •        •

Thr Glu Ser Cys Asp Lys His Tyr Trp Asp
ACAGAATCATGTGACAAGCACTATTGGGAT
        •          •         • env8 (661–720)

Ala Ile  Arg Phe Arg
                                     GCTATAAGGTTTAGA
                                                 •

Tyr Cys Ala Pro Pro Gly Tyr Ala Leu Leu Arg Cys Asn Asp Thr
TACTGTGCACCACCGGGTTATGCCCTATTAAGATGTAATGATACC
        •         •        700        •         • env9 (997–1044)

Lys Arg Pro Arg Gln Ala Trp Cys Trp Phe Lys Gly Lys
        AAAAGACCCAGACAAGCATGGTGCTGGTTCAAAGGCAAA
           1000        •         •         •

Trp Lys Asp
TGGAAAGAC env10 (1132–1215)

Lys Gly Ser Asp Pro Glu Val Ala Tyr Met Trp Thr Asn
        AAAGGCTCAGACCCAGAAGTAGCATACATGTGGACTAAC
                 •         •          •         •

Cys Arg Gly Gl

-continued

Glu Glu Met Leu Thr Ala
GAAGAGATTGCTGACCGCC
• •

Of the foregoing peptides, env1, and env2, env3 and gag1 are particularly contemplated for diagnostic purposes, and env4, env5, env6, env7, env8, env9, env10 and env11 are particularly contemplated as protecting agents. The foregoing peptides can be synthesized by conventional protein synthesis techniques, such as that of Merrified.

It will be apparent to those skilled in the art that various modifications and variations can be made in the processes and products of the present invention. Thus, it is intended that the present application cover the modifications and variations of this invention provided they come within the scope of the appended claims and their equivalents.

What is claimed is:

1. A nucleic acid selected from the group consisting of:

(1) env1, having nucleotides 1735–1809 of the envelope sequence of HIV-2, having the following sequence:

GTCAC TGCTA TAGAG AAGTA CCTAC AGGAC CAGGC

GCGGC TAAAT TCATG GGGAT GTGCG TTTAG ACAAG

TCTGC;

(2) env2, having nucleotides 1912–1983 of the envelope sequence of HIV-2, having the following sequence:

AGTAA AAGTT TAGAA CAGGC ACAAA TTCAG CAAGA

GAAAA ATATG TATGA ACTAC AAAAA TTAAA TAGCT

GG;

(3) env3, having nucleotides 1482–1530 of the envelope sequence of HIV-2, having the following sequence:

CCTAC AAAAG AAAAA AGATA CTCCT CTGCT CACGG

GAGAC ATACA AGA;

(4) env4, having nucleotides 55–129 of the envelope sequence of HIV-2, having the following sequence:

TGCAC CCAAT ATGTA ACTGT TTTCT ATGGC GTACC

CACGT GGAAA AATGC AACCA TTCCC CTGTT TTGTG

CAACC;

(5) env5, having nucleotides 175–231 of the envelope sequence of HIV-2, having the following sequence:

GATGA TTATC AGGAA ATAAC TTTGA ATGTA ACAGA

GGCTT TTGAT GCATG GAATA AT;

(6) env6, having nucleotides 274–330 of the envelope sequence of HIV-2, having the following sequence:

GAGAC ATCAA TAAAA CCATG TGTGA AACTA ACACC

TTTAT GTGTA GCAAT GAAAT GC;

(7) env7, having nucleotide 607–660 of the envelope sequence of HIV-2, having the following sequence:

AACCA TTGCA ACACA TCAGT CATCA CAGAA TCATG

TGACA AGCAC TATTG GGAT;

(8) env8, having nucleotide 661–720 of the envelope sequence of HIV-2, having the following sequence:

GCTAT AAGGT TTAGA TACTG TGCAC CACCG GGTTA

TGCCC TATTA AGATG TAATG ATACC;

(9) env9, having nucleotide 997–1044 of the envelope sequence of HIV-2, having the following sequence:

AAAAG ACCCA GACAA GCATG GTGCT GGTTC AAAGG

CAAAT GGAAA GAC;

(10) env10, having nucleotide 1132–1215 of the envelope sequence of HIV-2, having the following sequence:

AAAGG CTCAG ACCCA GAAGT AGCAT ACATG TGGAC

TAACT GCAGA GGAGA GTTTC TCTAC TGCAA CATGA

CTTGG TTCCT CAAT;

(11) env11, having nucleotide 1237–1305 of the envelope sequence of HIV-2, having the following sequence:

CGCAA TTATG CACCG TGCCA TATAA AGCAA ATAAT

TAACA CATGG CATAA GGTAG GGAGA AATGT ATAT;

and

(12) gag1, having nucleotide 991–1053 of the GAG sequence of HIV-2, having the following sequence:

GACTG TAAAT TAGTG CTAAA AGGAC TAGGG ATGAA

CCCTA CCTTA GAAGA GATGC TGACC GCC.

2. The nucleic acid of claim 1, wherein said nucleic acid is labeled with a compound selected from the group consisting of radioisotopes, enzymes, and fluorescent labels.

* * * * *